(12) United States Patent
Giles et al.

(10) Patent No.: US 10,088,451 B2
(45) Date of Patent: Oct. 2, 2018

(54) ION MOBILITY SPECTROMETER

(71) Applicant: Micromass UK Limited, Wilmslow (GB)

(72) Inventors: Kevin Giles, Stockport (GB); Martin Raymond Green, Bowdon (GB); John Brian Hoyes, Stockport (GB); Steven Derek Pringle, Darwen (GB); Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 305 days.

(21) Appl. No.: 14/785,936

(22) PCT Filed: Apr. 17, 2014

(86) PCT No.: PCT/GB2014/051224
§ 371 (c)(1),
(2) Date: Oct. 21, 2015

(87) PCT Pub. No.: WO2014/174260
PCT Pub. Date: Oct. 30, 2014

(65) Prior Publication Data
US 2016/0077054 A1    Mar. 17, 2016

(30) Foreign Application Priority Data

Apr. 24, 2013  (EP) .................................... 13165210
Apr. 24, 2013  (GB) .................................. 1307404.2

(51) Int. Cl.
G01N 27/62     (2006.01)
H01J 49/42     (2006.01)

(52) U.S. Cl.
CPC ........ G01N 27/622 (2013.01); *H01J 49/4265* (2013.01)

(58) Field of Classification Search
CPC combination set(s) only.
See application file for complete search history.

(56) References Cited

U.S. PATENT DOCUMENTS

| 5,572,022 A | 11/1996 | Schwartz et al. |
| 6,627,876 B2 | 9/2003 | Hager |
| 6,987,261 B2 | 1/2006 | Horning et al. |
| 7,683,314 B2 | 3/2010 | Green et al. |

(Continued)

FOREIGN PATENT DOCUMENTS

WO    WO 2007054712 A2 *  5/2007  ........... G01N 27/622

OTHER PUBLICATIONS

H.D. Zeman, "Deflection of an ion beam in the two-dimensional electrostatic quadrupole field", Rev. Sci. Instrum., vol. 48, No. 8, p. 1079-1085, Aug. 1977.

(Continued)

*Primary Examiner* — David E Smith
*Assistant Examiner* — Hsien Tsai

(57) ABSTRACT

A method of analyzing ions by ion mobility separation is disclosed. The method comprises controlling the amount of charge within an ion trap and then pulsing the ions from the ion trap into an ion mobility separator. This enables the charge injected into the ion mobility separator to be controlled and hence prevents space-charge interactions between the ions from distorting the ion mobility peaks detected by the detector.

19 Claims, 5 Drawing Sheets

(56) References Cited

U.S. PATENT DOCUMENTS

| 8,445,845 | B2 | 5/2013 | Green et al. |
| 8,481,921 | B2 | 7/2013 | Green et al. |
| 8,952,323 | B2 | 2/2015 | Bateman et al. |
| 2004/0200959 | A1* | 10/2004 | Kovtoun ............. H01J 49/4265 250/282 |
| 2010/0032561 | A1 | 2/2010 | Giles et al. |
| 2012/0119078 | A1 | 5/2012 | Green et al. |

OTHER PUBLICATIONS

Belov Et Al., "Multiplexed Ion Mobility Spectrometry—Orthogonal Time-of-Flight Mass Spectrometry", Anal Chem., vol. 79, No. 6, p. 2451-2462, Mar. 2007.

* cited by examiner

ION MOBILITY SPECTROMETER

CROSS-REFERENCE TO RELATED APPLICATION

This application is the National Stage of International Application No. PCT/GB2014/051224, filed 17 Apr. 2014 which claims priority from and the benefit of United Kingdom patent application No. 1307404.2 filed on 24 Apr. 2013 and European patent application No. 13165210.9 filed on 24 Apr. 2013. The entire contents of these applications are incorporated herein by reference.

BACKGROUND OF THE PRESENT INVENTION

In its simplest form an ion mobility separator (IMS) comprises a pulsed source of ions and a drift tube containing a buffer or drift gas. An electric field or travelling DC wave is applied along the drift tube so as to urge ions from an ion entrance to an ion exit of the drift tube. As the ions traverse the drift tube they separate according to their mobility through the buffer or drift gas. The velocity (v) of an ion having an ion mobility (K) in a drift tube with an applied electric field (E) is given by:

$$v = KE$$

Such devices have been constructed using ion guides in which the ions are confined by electrodes. AC voltages that oscillate at RF frequencies are applied to the electrodes so as to create a pseudo-potential force that confines the ions and allows highly efficient ion transmission through the ion guide.

Ions are typically pulsed into the IMS drift tube for analysis at periodic intervals that are spaced apart sufficiently to allow ions from one pulse to pass through the drift tube before ions in the next pulse enter the drift tube. In order maximise the duty cycle of such a device, it is known to receive and trap the ions from an ion source in an ion trapping region upstream of the IMS drift tube in the durations between the times that the ions are pulsed into the drift tube. Fewer ions are lost since ions are accumulated in the upstream ion trap during the time that a previously accumulated packet of ions is traversing the IMS drift tube. The separation time of a first pulse of ions in the IMS device is synchronised with the trapping and release times of the next pulse of ions into the IMS drift tube. This allows an ion transmission efficiency of nearly 100% to be achieved.

However, it is desired to provide an improved method of ion mobility separation and an improved ion mobility spectrometer, which preferably provide improved IMS peak widths and more reproducible drift times through the IMS drift tube.

SUMMARY OF THE PRESENT INVENTION

From a first aspect the present invention provides a method of analysing ions by ion mobility separation or mass separation comprising:

providing an ion mobility separator separation region (IMS) and an ion trap for releasing packets of ions into the IMS;

selecting a predetermined maximum charge desired to be released into the IMS in each packet of ions released from the ion trap into the IMS;

releasing a first packet of ions from the ion trap;

detecting the charge of ions in the first packet of ions using a detector;

determining a difference between the charge detected by the detector and said predetermined maximum charge; and releasing a second, subsequent packet of ions from the ion trap into the IMS, wherein the formation of the second packet of ions is controlled based on the difference between the charge detected in the first packet of ions and the predetermined maximum charge, such that the charge of ions in the second packet of ions is substantially the same or less than said predetermined maximum charge.

The inventors have recognised that the resolution of an ion mobility spectrometer and the reproducibility of the IMS drift times can be improved by avoiding the ions repelling each other on entry into the IMS device and during their subsequent passage through the IMS separation region. The present invention limits the charge entering the separation region (i.e. RF confined drift tube) and hence avoids deterioration of IMS performance due to the ions repelling each other. Specifically, the amount of charge entering the separation region is limited by controlling the amount of charge released into the separation region from an upstream ion trap.

It has also been recognised that if a relatively large number of ions having a similar ion mobility pass through the separation region then these ions may repel each other as they travel along the separation region and cause broadening of the IMS peaks. Preferred embodiments of the present invention overcome such a problem.

It is known to limit the charge density in ion traps and mass analysers that store ions in order to avoid space-charge effects therein. For example, WO 2004/068523 discloses a method that restricts the amount of charge transmitted from an ion trap into a downstream ion storage mass analyser, in order to avoid space charge effects in the ion storage mass analyser. However, the space-charge effects that are prevalent in ion traps and ion storage mass analysers have not been considered to be relevant to IMS devices for several reasons. For example, ion traps and ion storage mass analysers inherently urge ions together in a relatively small volume in which space-charge effects are prevalent, whereas IMS devices act to separate out ions, and so it is not obvious that the considerations of space-charge effects apply to IMS devices.

Also, the manifestation and mechanism of space-charge effects in ion storage devices are not present in IMS devices. Space-charge effects in ion storage devices employing mass selective ejection methods cause mass shifts that result in loss of mass measurement accuracy and mass resolution. This is due to the ions experiencing an additional potential due to the ionic environment, which distorts the confining electric field. This distortion leads to a change in the secular frequency of each ion and hence a change in the apparent mass to charge ratio of the ion. This does not occur in an IMS device, which does not confine ions in a small region during analysis and does not rely on resonant frequencies for analysis.

Also, most of the historical data obtained from IMS drift tubes relates to non-radially confined drift tubes. Any space-charge effects in such devices would cause the ion cloud to expand radially and would not have a significant effect on the drift times measured by the device. Such space-charge effects would therefore go unrecognised.

Furthermore, space-charge effects in ion storage devices are caused by the total number of ions present in the trapping region. This is quite different to the recognition that in an IMS device the ions of similar mobility remain in narrow spatial distributions as they traverse the IMS separation region and that this may cause local space-charge effects in regions where many ions have similar ion mobilities. In some situations the population of ions within a specific mobility region must be controlled regardless of the total number of ions released into the IMS device.

For at least the above reasons, methods for reducing space-charge effects in ion storage devices have not been applied to IMS devices. Therefore, it has not previously been recognised that IMS devices may benefit from controlling the amount of charge entering the device in the manner claimed in the present invention.

According to the present invention, packets of ions are preferably repeatedly pulsed into the IMS device.

Ions are preferably permitted to enter and become trapped in the ion trap during ion accumulation periods, wherein the first packet of ions is accumulated within the ion trap over a first accumulation period and the second packet of ions is accumulated within the ion trap over a second accumulation period. The duration of the second accumulation period may be selected or altered relative to the first accumulation period based on the difference between the charge of the ions detected in the first packet of ions and the predetermined maximum charge.

The duration of the second accumulation period may be reduced relative to the first accumulation period if the charge detected in the first packet of ions is above the predetermined maximum charge. This allows less ions to enter the ion trap during the second accumulation period and so decreases the charge of the ions in the second packet. Alternatively, the duration of the second accumulation period may be increased relative to the first accumulation period if the charge detected in the first packet of ions is below the predetermined maximum charge. This allows more ions to enter the ion trap during the second accumulation period and so increases the charge of the ions in the second packet.

The ions are directed into the ion trap at an ion fill rate and are preferably trapped in said ion trap during ion accumulation periods. The first packet of ions may be accumulated within the ion trap at a first ion fill rate and the second packet of ions may be accumulated in the ion trap at a second ion fill rate. The second fill rate may be selected or altered relative to the first fill rate based on the difference between the charge of the ions detected in the first packet of ions and the predetermined maximum charge.

The second fill rate may be reduced relative to the first fill rate if the charge detected in the first packet of ions is above the predetermined maximum charge. This allows less ions to enter the ion trap during the accumulation period of the second packet of ions and so decreases the charge of the ions in the second packet. Alternatively, the second fill rate may be increased relative to the first fill rate if the charge detected in the first packet of ions is below the predetermined maximum charge. This allows more ions to enter the ion trap during the accumulation period of the second ion packet and so increases the charge of the ions in the second packet.

Each of the accumulation periods may have the same, constant duration.

The different fill rates may be achieved by attenuating the ions travelling towards the ion trap by different amounts.

Only a portion of the ions in the ion trap may be ejected during the release of each packet of ions from the ion trap. The size of the portion ejected in said second packet of ions may be selected or altered relative to the size of the portion ejected in the first packet of ions based on the difference between the charge of the ions detected in the first packet of ions and the predetermined maximum charge.

The first packet of ions may pass through the IMS and then to the detector. Ions are preferably driven through the IMS by an electric field and the ions in the first packet of ions may be driven through the IMS at a higher force and the ions in the second packet of ions may be driven through the IMS at a lower force. This enables the first packet of ions to be swept through the IMS relatively quickly, which is acceptable since the first packet of ions is primarily for charge detection and so these ions need not be well separated in the IMS. The second packet of ions passes through the IMS at a slower rate and so the ions in this packet become well separated, enabling their ion mobilities to be well resolved.

A mass analyser may be provided downstream of the IMS and upstream of the detector for mass analysing ions that have passed through the IMS. The mass analyser may be operated in a first mode such that the first packet of ions is substantially unattenuated by the mass analyser or wherein the first packet of ions bypasses the mass analyser and then passes to the detector; and the mass analyser may be operated in a second mode such that the second packet of ions is attenuated by the mass analyser during mass analysis therein or wherein the second packet of ions does not bypass the mass analyser. This allows the unattenuated charge of the ions in the first packet of ions to be determined, even in the presence of the mass analyser.

Alternatively, a mass analyser and said detector may be provided downstream of the IMS; the first packet of ions may be directed to the detector without passing to the mass analyser; and the second packet of ions may be directed to the mass analyser.

Alternatively, the detector may be provided upstream of said IMS and said first packet of ions may be released from the ion trap to the detector. This enables the charge to be detected relatively quickly, as the first packet of ions need not traverse the IMS.

The method may further comprise detecting the charge of ions in the second packet of ions using a detector; determining a difference between the charge of the ions detected in the second packet of ions and the predetermined maximum charge; and releasing a third, subsequent packet of ions from the ion trap to the IMS; wherein the formation of the third packet of ions is controlled based on the difference between the charge detected in the second packet of ions and the predetermined maximum charge, such that the charge of ions in the third packet of ions is substantially the same or less than said predetermined maximum charge.

The predetermined maximum charge may be the total charge desired to be pulsed into the IMS for all ions in a packet of ions. In this case, the total charge of all of the ions in the first packet of ions is detected by the detector.

Alternatively, the predetermined maximum charge may be the maximum amount of charge of ions within a predetermined range of drift times through the IMS that is desired to be pulsed into the IMS in a packet of ions. In this case, the first packet of ions is detected by the detector after the ions have passed through the IMS, wherein the detector determines the amount of charge of ions in the first packet of ions that have drift times within said predetermined range of drift times, and wherein this detected charge is compared to the predetermined maximum charge and the comparison is used to control the formation of the second packet of ions such that ions in the second packet of ions that have drift times within the predetermined range of drift times have a total charge that is substantially the same or less than the predetermined maximum charge.

Alternatively, the predetermined maximum charge may be the maximum amount of charge of ions within a predetermined range of drift times through the IMS that is desired to be pulsed into the IMS in a packet of ions; wherein ions having said predetermined range of drift times are assumed to have a predetermined range of mass to charge ratios; wherein the first packet of ions is mass analysed and the total charge of ions within this packet having said predetermined range of mass to charge ratios is detected; and wherein this detected charge is compared to the predetermined maximum charge and the comparison is used to control the formation of the second packet of ions such that the ions in the second packet of ions that have drift times within the predetermined range of drift times have a total charge that is substantially the same or less than the predetermined maximum charge.

The ion trap is preferably not continuously filled for the duration between pulses into the IMS.

From a second aspect the present invention provides a method of analysing ions by ion mobility separation or mass separation comprising:

providing an ion mobility separator separation region (IMS) and an ion trap for releasing packets of ions into the IMS;

selecting a predetermined maximum charge desired to be released into the IMS in each packet of ions released from the ion trap;

directing ions from an ion source to a detector and detecting the rate at which charge is received at the detector due to ions from the ion source being detected;

directing ions from the ion source into the ion trap and trapping the ions only during an ion accumulation period;

selecting the duration of the ion accumulation period or controlling the attenuation of ions travelling towards the ion trap during the accumulation period such that the charge of the ions trapped within the ion trap is substantially the same or less than said predetermined maximum charge; and releasing the ions from the ion trap into the IMS.

The ion source may generate a continuous ion beam that is diverted between the detector and ion trap.

The detector is preferably provided upstream of said IMS.

The predetermined maximum charge is preferably the total charge desired to be pulsed into the IMS for all ions in a packet of ions.

The ion trap is preferably not continuously filled for the duration between pulses into the IMS.

The method may further comprise operating in a first mode of operation wherein first electric field conditions are applied within the IMS such that ions passing through the IMS separate according to their ion mobilities and/or operating in a second mode of operation wherein second electric field conditions are applied within the IMS such that ions passing through the IMS separate according to their mass to charge ratios.

The present invention may be used to analyse ions by separating the ions according to their ion mobilities and/or their mass to charge ratios within the IMS separation region. If first electric field conditions are applied across the IMS separation region then the ions passing through the buffer gas in the separation region will separate according to their ion mobilities. In contrast, if second electric field conditions are applied across the IMS separation region then the ions passing through the buffer gas in the separation region will separate according to their mass to charge ratios. The analyser may be operated in either one of the modes or may be switched between the two modes so as to perform one mode and then the other mode.

For example, an electric field may be continuously arranged along the separation region so as to drive ions through the buffer gas in the separation region and cause the ions to separate according to their ion mobilities. In this mode the ions travel through the separation region at a substantially steady state velocity that depends on their ion mobilities within the buffer gas.

Alternatively, an electric field may be intermittently arranged along the separation region by applying a pulsed voltage to the separation region so as to drive ions through the separation region and such that ions passing through the separation region separate according to their ion mobilities. In this mode, the ions are prevented from reaching their steady state velocity as they pass through the buffer gas in the separation region because the electric field that drives the ions through the separation region is pulsed on and off. The velocity of an ion passing through the separation region therefore decays before the next pulse is applied. This results in the ions separating according to their mass to charge ratios as they pass through the separation region.

It is contemplated that a potential barrier or well may be conveyed along the separation region in order to drive ions through the buffer gas. In the first mode, a relatively slow moving potential barrier or well may be used to drive ions through the separation region, resulting in the ions separating according to their ions mobilities as they pass through the separation region. In the second mode, a relatively faster moving potential barrier or well may be used to drive ions through the separation region, resulting in the ions separating according to their mass to charge ratios as they pass through the separation region.

The separation region may be operated so as to achieve ion mobility separation or mass to charge ratio separation according to the techniques disclosed in US 2010/0032561.

The present invention also provides an ion mobility spectrometer or mass spectrometer arranged and configured and having control means so as to perform any one of the methods described above.

Therefore, the present invention provides an ion mobility spectrometer or mass spectrometer comprising:

an ion mobility separator separation region (IMS), an ion trap for releasing packets of ions into the IMS, and a detector; and control means arranged and adapted to:

release a first packet of ions from the ion trap;

detect the charge of ions in the first packet of ions using the detector;

determine a difference between the charge detected by the detector and a predetermined maximum charge desired to be released into the IMS in each packet of ions released from the ion trap into the IMS; and release a second, subsequent packet of ions from the ion trap into the IMS, wherein the formation of the second packet of ions is controlled based on the difference between the charge detected in the first packet of ions and the predetermined maximum charge, such that the charge of ions in the second packet of ions is substantially the same or less than said predetermined maximum charge.

The present invention also provides an ion mobility spectrometer or mass spectrometer comprising:

an ion source, an ion mobility separator separation region (IMS), an ion trap for releasing packets of ions into the IMS, and a detector; and control means arranged and adapted to:

direct ions from the ion source to the detector and detect the rate at which charge is received at the detector due to ions from the ion source being detected;

direct ions from the ion source into the ion trap and trap the ions only during an ion accumulation period; and select the duration of the ion accumulation period or control the attenuation of ions travelling towards the ion trap during the accumulation period such that the charge of the ions trapped within the ion trap is substantially the same or less than a predetermined maximum charge desired to be released into the IMS in each packet of ions released from the ion trap; and release the ions from the ion trap into the IMS.

The mass spectrometers may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometers may further comprise either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The mass spectrometers may further comprise a device arranged and adapted to supply an AC or RF voltage to the electrodes. The AC or RF voltage preferably has an amplitude selected from the group consisting of: (i)<50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i)<100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENTS

Figure 1:
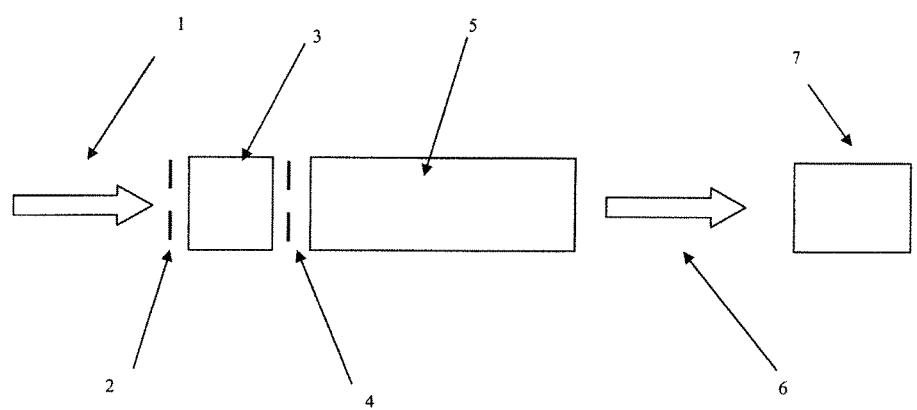
FIG. 1 shows an ion mobility spectrometer according to a first embodiment of the present invention.

FIG. 1 shows a block diagram of an ion mobility spectrometer according to a preferred embodiment. The device comprises an entrance gate electrode 2, an ion trapping region 3, an ion mobility separator (IMS) drift tube 5 and a detector 7. During operation, an ion beam 1 is received by the apparatus. This beam may be a continuous or discontinuous beam of ions. The beam 1 may be received directly from an ion source or may pass through analytical devices or fragmentation/reaction regions upstream of the trapping region 3.

Preferably, the trapping region 3 is an RF confined ion guide. The trapping region may be a rod set or a stacked ring design or a coaxial structure. The trapping region 3 is preferably maintained at a pressure of 0.1 to 10 torr by introduction of a buffer gas.

According to a mode of operation known in the art, ions are first allowed to fill an the trapping region 3 during an accumulation period. During this period, the potential applied to entrance gate electrode 2 is such that ions 1 can enter the ion trapping region 3, whilst the exit gate electrode 4 is set to a potential such that ions which enter the trapping region 3 cannot exit. After an accumulation time T1, the potential applied to entrance gate electrode 2 is changed such that ions substantially cannot enter the trapping region 3. Simultaneously, or after a delay time, the potential applied to the exit gate electrode 4 is changed such that ions are free to exit the trapping region 3. Ions are then driven out of the trapping region 3 into the IMS separation drift tube 5. Ions may be driven into the IMS device 5 by a DC field acting to urge ions to travel in the direction from the entrance to the exit of the trapping region 3, by a DC travelling wave, by a pseudo-potential driving force, or by a flow of the buffer gas.

Ions enter the IMS drift tube 5 with a relatively low temporal and spatial spread. Once all the ions have left the trapping region 3 the potential applied to exit gate electrode 4 is changed such that no further ions can exit the trapping region 3 and the potential applied to entrance gate electrode 2 is changed such that a next population of ions start to accumulate in the trapping region 3. Simultaneously, or after a short delay time, ions are urged down the ion mobility drift tube 5 by application of a DC field or travelling wave. The drift tube 5 is preferably an RF confined ion guide constructed of rod sets or stacked rings and operated at elevated pressure. While the first population of ions are separating according to their drift times in the IMS device 5, a second set of ions is being accumulated in the trapping region 3. When all the ions have exited the IMS drift tube 5, or when the predetermined IMS separation time in complete, the second set of ions in released from the trapping region 3 into the IMS separation device 5 and a third set of ions is accumulated in the ion trap 3.

Ions 6 which exit the IMS separation device 5 are recorded on a detector 7. Ions may pass through further analytical or fragmentation/reaction regions before being recorded at the detector 7.

According to conventional techniques, the duration of the trapping period in the ion trap 3 is constant and is synchronized to the cycle time of the IMS separation with the drift tube 5. The ion trap 3 is used to improve the duty cycle of the device by capturing ions in between the IMS separation cycles. However, it has been recognised that such techniques may lead to a high charge density of ions building up in the ion trap 3 and when the ions are subsequently released from the ion trap 3 into the IMS drift tube 5 the charge density of the ions may alter the drift times of the ions and broaden the IMS peak widths.

According to a preferred embodiment of the present invention the charge density of the first population of ions which have passed through the IMS separation device 5 and have been detected using detector 7 is used, either on its own or in conjunction with previously recorded data, to control the accumulation time of a subsequent population of ions in the ion trapping region 3. This accumulation time may be controlled such that the total charge density entering the IMS device 5 from the ion trapping region 3 does not exceed a predetermined maximum value, such that the analytical performance of the IMS device 5 is not compromised.

For example, in operation a first population of ions P(1) is accumulated in trapping region 3 for time T1. This first population of ions is pulsed into the IMS drift tube 5 and whilst IMS separation occurs over time period T(IMS) a second population of ions P(2) is accumulated in ion trap 3 for a time T2, where T2=T(IMS). The charge density of the first population of ions I(1) is measured at the detector 7 and used to calculate the accumulation time T3 required to ensure that the estimated charge density I(3) accumulated in the ion trap 3 for a third population of ions P(3) will be within a predetermined limit I(L); where:

$$T3 = T1 * \frac{I(L)}{I(1)}$$

The maximum accumulation time allowed T(max) if preferably equal to T(IMS).

After the first population of ions has been analysed by the IMS device 5 and detector 7, the second population of ions is then injected into the IMS device 5 and the third population of ions P(3) is accumulated in the ion trap 3 for time T3. Time period T3 may be less than T1 so as to reduce the charge density of the third ion population relative to the first ion population.

After ions have been accumulated in the ion trap 3 for time T3, these ions may be held in the ion trap for a further time period time T(IMS)−T3 before being released into the IMS drift tube 5. This ensures that the third population of ions does not enter the drift tube 5 until the second population of ions has been separated within the drift tube 5. In general:

$$Tn = T(n-2) * \frac{I(L)}{I(n-2)}$$

where Tn represents the accumulation time for the nth population of ion within the ion trap 3; T(n−2) represents the accumulation time for the (n−2)th population of ions within the ion trap 3; I(L) represents the predetermined limit of charge density desired to enter the IMS flight tube 5; and I(n−2) represents the charge density of the (n−2)th population of ions.

This feedback control of the accumulation time of trapping region 3 may continue for many IMS cycles during the duration of the experimental time. The accumulation time of the ion trap 3 may vary between a maximum time T(max) that is substantially equal to the IMS drift time, and a minimum accumulation time T(min). If T(n)>T(max), then T(n) is set to T(max). If T(n)<T(min), then T(n)=T(min).

The present invention also contemplates other methods for controlling the population of ions entering the IMS separation device. For example, instead of basing the prediction of the ion population in a subsequent accumulation on data from a single recorded data set, several previously recorded data sets may be used to examine a trend in the data and predict the charge density of a subsequent population of ions and hence adjust the accumulation time of this subsequent population based on this prediction.

In the exemplary method described, data from a single IMS separation experiment is used to adjust the population for a subsequent single IMS separation. However, it may be preferable to average or sum data from a set of multiple IMS experiments, each of which is taken using substantially the same accumulation time, and then use this data to predict the accumulation time for a subsequent set of IMS data.

IMS separation may be combined, or nested with chromatographic separation such as liquid or gas chromatography (LC or GC) to produce a multi-dimensional data set with high peak capacity.

In the case of LC chromatographic, peaks may be 1 to 10 seconds wide at the base. To sample or record a chromatographic peak effectively it is advisable to record at least 10 sample points during the elution time. Therefore, for a 1 second chromatographic peak data should be recorded at 100 ms intervals. IMS separation times may be in the order of 10 ms with individual mobility peaks 1 ms wide or less. Therefore, a single 100 ms sample can be recorded as the sum or average of ten IMS separations. Each of these ten IMS separations may be performed with substantially the same ion accumulation time and the accumulation time may then be changed for a subsequent ten IMS cycles based on the total charge density recorded during the initial ten IMS cycles.

Figure 5:
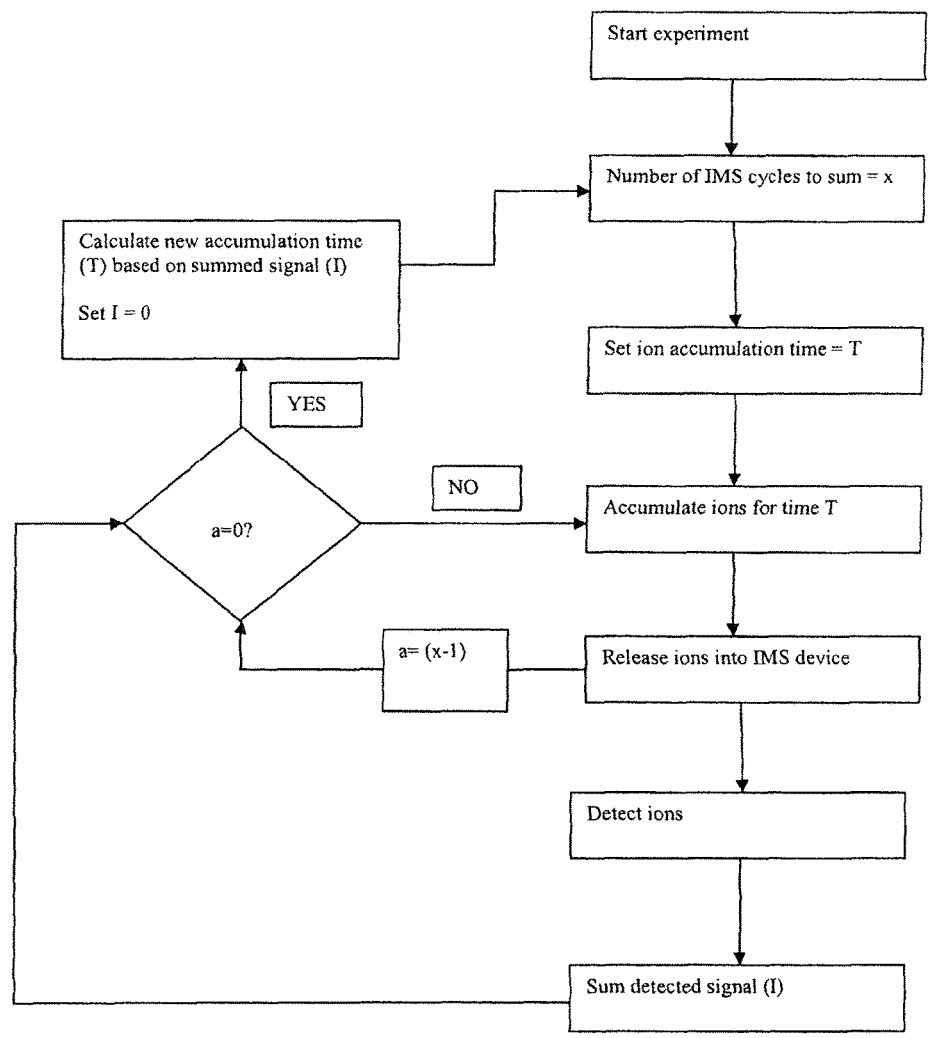
FIG. 5 shows a flow chart illustrating part of a method according to a preferred embodiment of the present invention.

A flow diagram representing the generalised feedback routine described above is shown in FIG. 5.

Another embodiment of the invention is to collect data from a short survey experiment to determine the charge density of the incoming ion beam prior to each IMS separation or group of IMS separations. This survey data can be used to adjust the accumulation time for a subsequent IMS separation cycle. For example, the survey experiment may consist of filling the trapping region 3 for a predetermined short accumulation time. This ion population may then be injected into the IMS device and caused to traverse the length of the drift tube 5 and become incident on the detector 7. This data can then be used to predict the accumulation time for a subsequent accumulation. In this embodiment, a subsequent population of ions may not be accumulated during the time that ions from the survey data are traversing the drift region. This can lead to a reduced duty cycle and lower overall efficiency of sampling of the ions produced in the ion source.

In order to improve the duty cycle in this embodiment, the transit time of ions through the drift tube 5 can be decreased by increasing the driving force through this region 5 during the survey experiment. When using a DC driving force, the DC field may be increased in order to decrease the transit time of the ions through the drift tube. Alternatively, if a travelling DC wave is used to drive ions through the drift tube 5, then the amplitude of the travelling wave may be increased or the velocity of the travelling wave may be decreased such that ions travel substantially with the travelling wave front independent of the mobilities of the ions. Changing the driving force during the survey scan in this way degrades the IMS resolution during the survey scan. However, as this data is only used to calculate the charge density, ions need not be well separated during the survey scan. In this manner, the time in which the survey scan may be competed may be reduced to a small fraction of the time taken for an analytical IMS separation and so the duty cycle of the experiment is reduced by only a minimal amount when conducting the survey scan.

An alternative method is contemplated wherein a survey scan may be performed without trapping ions in the upstream trapping region. In this method a continuous beam of ions from the ion source is accelerated through the IMS drift region 5 and the charge density of the ions is recorded by the detector 7. The charge density recorded during this survey experiment may be used to calculate and set the desired accumulation time for a subsequent IMS experiment or group of IMS experiments.

Figure 2:
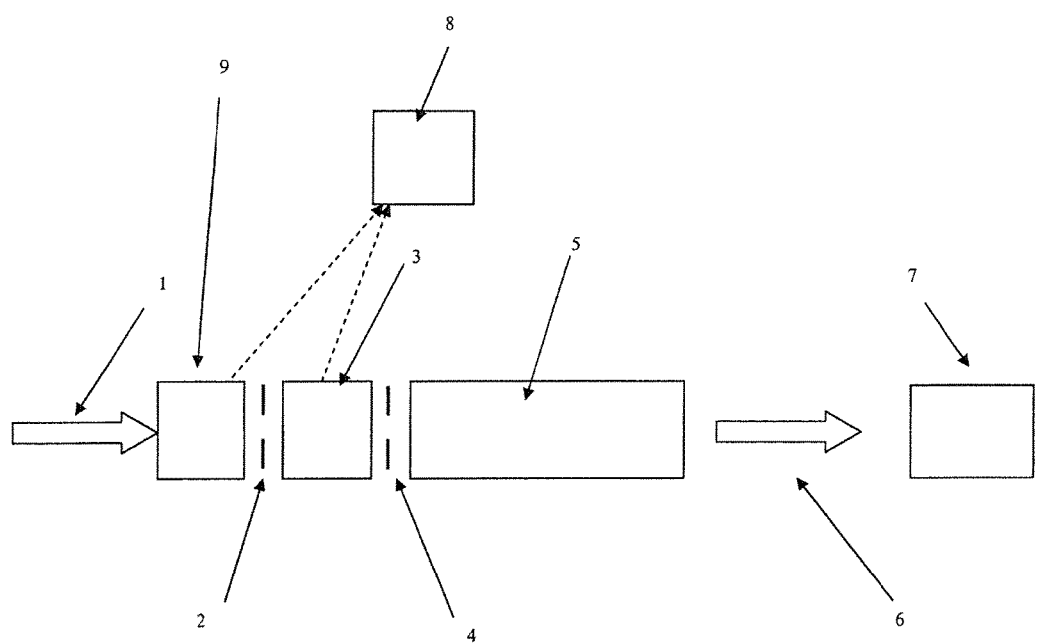
FIG. 2 shows an ion mobility spectrometer according to a second embodiment of the present invention.

FIG. 2 shows another embodiment of the present invention that is similar to that of FIG. 1 and wherein like reference numerals designate corresponding apparatus. In the embodiment shown in FIG. 2, an electrode assembly 9 is positioned upstream of the ion trap 3 and a second ion detector 8 is positioned upstream of the IMS device 5.

In operation a survey data set is recorded in order to determine the charge density in the incoming ion beam 1 by directing a portion of the ions to ion detector 8. The ion beam 1 may be a continuous ion beam and the electrode assembly 9 may be used to switch the ions between being received at the ion trap 3 and the detector 8. When the ions are received at the detector their charge density per unit time can be measured. This value can then be used to determine the accumulation time for ions to be subsequently accumulated in the ion trap 3 so as to prevent the charge density of ions introduced into the IMS device 5 from becoming too high. The survey of the incoming charge density using detector 8 may be performed during part of the period while ions are being separated in the IMS device 5 and detected on detector 7. In this way, the duty cycle of the overall experiment can be maximised.

A pulsed lens assembly such as that described in U.S. Pat. No. 7,683,314 may be utilised for the electrode assembly 8. In this disclosure the ion beam is switched between full transmission and zero transmission with variable duty cycle. It is contemplated that the ions be directed towards the detector 8 during the low or zero duty cycle part of the transmission cycle. The signal detected on detector 8 can then be used to dynamically adjust the duty cycle of the attenuation lens and/or the number of cycles of the pulsed attenuation lens during a fixed accumulation time of the ion trapping region 3. Other types of attenuation devices may be used.

Electrode assembly 9 may be used to direct a known and small percentage of the incoming ions towards detector 8 whilst directing the remainder of the ions towards the trapping region 3. The accumulation time in trapping region 3 may then be altered based on the signal detected by detector 8. Alternatively, survey data may be acquired by accumulating ions in trapping region 3 for a short period of time and then releasing these ions to be detected by detector 8, rather than passing the ions through the IMS separating region 5. This can be an advantageous mode of operation as the transit time of ions from the trapping region 3 to detector 8 may be less than from trapping region 3 to detector 7. This allows the survey scan to be performed over a shorter period of time relative to the IMS separation time and hence increases the overall duty cycle of the acquisition.

Detector 8 may be a destructive detector, such as an electron multiplier or Faraday plate, or a non destructive detector such as an inline inductive charge detector.

The IMS device 5 may be combined with a further upstream analytical device such as a quadrupole mass filter or a differential ion mobility filter. Additionally, or alternatively, the IMS device 5 may be combined with one or more downstream analytical devices, such as a quadrupole mass filter or a time of flight mass analyser. However, it is important to note that when used in conjunction with a second downstream device which restricts the total charge transmitted, such as a resolving quadrupole mass filter, the signal reaching the ion detector 7 may not be representative of the charge density entering the IMS device 5. In order to overcome this problem, the second downstream device may be switched to a mode to allow full transmission of a population of ions which is representative of the population of ions prior to the second downstream device or a separate ion detector may be placed upstream of the second downstream device to measure the charge density of the ions.

Figure 3:
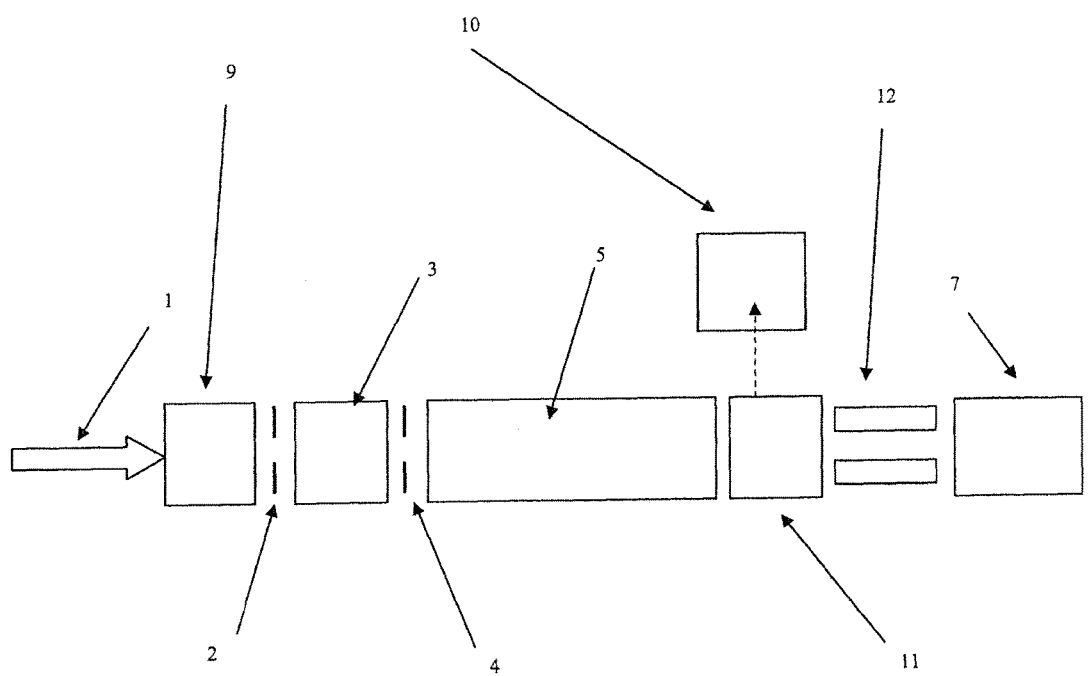
FIG. 3 shows an ion mobility spectrometer according to a third embodiment of the present invention.

FIG. 3 shows an embodiment wherein a mass analyser is arranged downstream of the drift tube 5. The embodiment in FIG. 3 is similar to that of FIG. 2 and like elements are indicated by the same reference numerals. In the embodiment of FIG. 3, a resolving quadrupole mass filter 12 is positioned after IMS drift tube 5. When the mass filter 12 filters ions, the ion current recorded at detector 7 will not be representative of the charge density of the incoming ion beam 1. The device may be operated in a survey mode in which the quadrupole rod set 12 is set to an RF only mode so as to transmit ions of all mass to charge ratios. The signal measured at detector 7 can then be used to control the accumulation time of the ion trapping region 3.

As an alternative to operating the mass filter 12 in a non-filtering mode, an additional detector 10 may be arranged downstream of the IMS drift tube 5 so that ions can be passed to the detector 10 without having to be transmitted through the mass filter. During a survey scan, a switching or diverting electrode arrangement 11 may be used to direct ions exiting the IMS drift tube 5 to detector 10. The signal recorded on detector 10 can then be used to adjust the accumulation time of ions in ion trapping region 3.

Figure 4A:
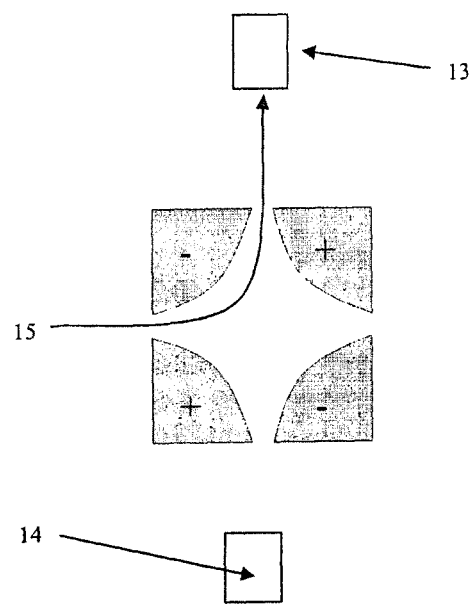
FIGS. 4A and 4B show a switching device for switching a beam of ions between an ion detector and an ion analyser.
Figure 4B:
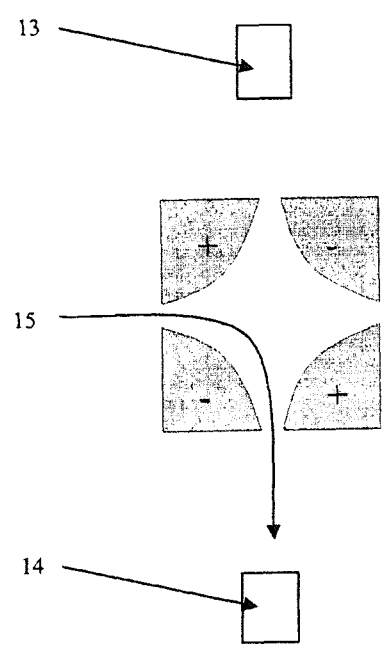

FIGS. 4A and 4B show an embodiment of a device that may be used to switch ions between an ion detector and analyser. Such a device may be used to switch ions to the detector 8 in the embodiment of FIG. 2 or to switch ions to the detector 10 in the embodiment shown in FIG. 3. FIGS. 4A and 4B show a representation of a quadrupolar electrostatic lens such as that described in Rev. Sci. Instrum., Vol. 48, No. 8, August 1977. This device comprises four electrodes with hyperbolic inner electrode surfaces. FIG. 4A shows the device in a mode where the incoming ion beam 15 is directed towards and ion detector 13. FIG. 4B shows the device in a mode of operation where the incoming ion beam 15 is directed towards a downstream analyser 14. Other ways of splitting or diverting the ion beam are also envisaged.

In the embodiments described above the total charge entering the upstream trapping region 3 is controlled within a predefined value. However, in some instances the performance of the IMS device may not be distorted significantly by the overall charge density entering the flight tube, but may be distorted due to the charge density within a specific range of ion mobilities. Ions with mobilities outside this range may not be distorted significantly, even though the total population of ions within the IMS device is large. This effect arises due to the differences in time over which groups of ions from different species are in close proximity within the IMS drift tube. For example, if a population of ions released into the drift tube is made up of ions from many different analyte species, all of these ions reside within the drift tube within a narrow band only at the point of ion injection. As these ions are urged along the drift tube they separate from each other into distinct bands or regions of the drift tube. However, portions of the ion population which have similar ion mobilities stay within a narrow band and hence remain in close proximity for a large portion or all of the length of the drift tube. The space-charge interaction effects on these ions can be large, particularly if there is a high charge density in this mobility range. Portions of the ion population with lower charge densities and different mobilities which separate away from species with high charge density may experience the effects of space-charge interaction for a shorter time period and therefore the distortions in the peak shape and/or the shifts in the drift times are not as severe for these species.

In this case, rather than controlling the total charge injected into the drift tube, it is desirable to control the charge density within a specific drift time range. Any of the methods described to control the total charge density injected into the drift tube 5 may be utilised, although the charge must be measured after IMS separation has occurred. Several embodiments of this method are envisaged.

For example, detector 7 or 10 may be used to record an IMS drift chromatogram and the total charge density within a specific region or regions of this chromatogram may be measured and used to control the accumulation time of ions in the ion trapping region 3 or the attenuation of ions prior to the trapping region 3 during a fixed accumulation time. Alternatively, a gate electrode may be arranged after the IMS device 5 so that only a selected drift time region or a plurality of drift time regions are allowed to reach detector 7 or 10 during an IMS cycle. In this case, the data recorded from multiple drift time regions may be summed into a single charge density value or may be interrogated separately. In both of these cases, it is the intention to keep the charge density of an ion population with a specific mobility or drift time through the IMS device within a predefined maximum value by altering the conditions during the accumulation period. This may also be combined with controlling the maximum value of the total charge injected into the trapping region. However, this maximum total charge is larger than the charge allowed for a specific drift time region.

It should be noted that when the IMS device 5 is used in conjunction with a downstream mass analyser, the charge density recorded within a specific range of mass to charge ratios may be used to infer or estimate the charge density within a specific drift time range. This is because of the strong positive correlation between mass to charge ratio and IMS drift time.

When the IMS device is coupled to a downstream analyser, for example a time of flight analyser, it is preferable to use a measure of charge density within a specific range or ranges of mass to charge ratio to control the total population of ions entering the IMS device such that the peak shape and/or drift time measurement in a specific drift time range or ranges is not compromised due to space-charge interactions within the IMS device.

In all the cases discussed it is preferable to record a value representative of the attenuation of the ion population which has been applied. This value may be used to re-scale the intensity of the data recorded during the acquisition to represent the intensity of the incoming ion beam before attenuation. This enables the quantitative performance of the system to be maintained even though some ions have been discarded.

Although the present invention has been described with reference to preferred embodiments, it will be understood by those skilled in the art that various changes in form and detail may be made without departing from the scope of the invention as set forth in the accompanying claims.

For example, it should be noted that although the ions have been described as being accumulated in the upstream trapping device 3 only once per IMS cycle, the invention also contemplates a mode such that ions are delivered to the trapping region 3 or allowed to enter the trapping region 3 as a series of one or more ion packets during a fixed or variable accumulation time.

In the case where there is a fixed accumulation time, the continuous incoming ion beam may be switched or gated between high transmission and low transmission with a variable duty cycle during the accumulation time. The duty cycle of the gating electrode can be altered to result in the desired charge density being accumulated in the trapping region to allow control of the ion population released into the IMS device 5. Such a gating device and method of accumulation of a population of ions into a trap is described in US 2012/0119078. It is advantageous that the number of separate gated periods during the accumulation time is reproducible. Therefore number of accumulation periods and the total accumulation period, and hence the IMS cycle time, are preferentially synchronised such that a reproducible integer number of ion beam gating periods occur per total accumulation time period.

Although it is preferable for the gating period or periods to be synchronised to the IMS separation cycle time, it is also contemplated that the accumulation period or periods may not be synchronised to the IMS separation cycle time. In this case, there may be some uncertainty in the charge density accumulated in the trapping region 3 prior to injection into the IMS device 5. If the uncertainty or error in the time in which ions are allowed to fill the trapping region 3 is small compared to the total accumulation time, the methods described will still control the ion population satisfactorily and without deviating from the spirit of the invention.

In another method, ions may be accumulated for a fixed time period and an upstream attenuation device such as a defocusing lens may be used to attenuate the incoming ion beam such that a target charge density injected into the IMS separator is not exceeded.

In another method, ions may be accumulated for a fixed time in the upstream ion trapping region but only a portion of the total charge density within the trapping region is released into the IMS device. The amount of charge released from the trapping region can be controlled to be within a predefined maximum, for example, by using the methods previously described. This may be achieved by providing a gate electrode at the exit of the trapping region and pulsing the gate electrode potential one or more times such that ions are allowed to exit the trapping region for a variable time period. Alternatively, the ion population within the trapping region can be divided into several populations of known charge density and only a certain number of these sub populations may then be released into the IMS device. The ion population may be partitioned within a segmented RF confined ion guide by application of DC potentials to some of the segments to form multiple axial DC potential wells.

The invention can be used to control the ion population, and hence reduce the effects of space-charge interactions, for ions introduced into a multiplexed ion mobility device such as that described in Anal Chem. 2007 Mar. 15; 79(6): 2451-2462. MULTIPLEXED ION MOBILITY SPECTROMETRY-ORTHOGONAL TIME-OF-FLIGHT MASS SPECTROMETRY Belov Et Al. A fixed number of ion packets can be released into the IMS device per cycle rather than varying the number of ion packets introduced per IMS cycle so as to control the charge density of each packet.

The invention disclosed may be combined with an upstream high capacity ion trap with mass selective ejection of ions. An example of such an apparatus is described in PCT/GB2008/002981 or U.S. Ser. No. 12/676,154. In this application a high capacity, low performance analytical ion trap is placed upstream of a high performance, low capacity analytical ion trap. An attenuation device is placed between the two traps. In operation ions are mass selectively ejected from the upstream low performance ion trap into the high performance trap and ions are substantially simultaneously ejected from the higher performance ion trap and detected, thus producing a mass spectrum. This results in the upstream analytical ion trap only containing a portion of the total population of ions at any time during its analytical scan. This reduces the likelihood of the analytical performance of this second ion trap being compromised due to space-charge interactions. Additionally, once a survey mass spectrum has been acquired either by mass selective ejection from either or both ion traps, the transmission of portions of the total ion population with different mass to charge ratios exiting the upstream ion trap may be dynamically adjusted such that the population of ions in the downstream analytical ion trap does not exceed a predefined upper limit during any part of this linked scanning process.

This low performance analytical ion trap and attenuation device may be placed upstream of the trapping region 3.

Based on a mass to charge ratio survey scan of the population of ions in the upstream trapping device and the known correlation between mass to charge ratio and IMS drift time, the attenuation lens may be dynamically changed such that the charge density within a specific mass to charge ratio range (and hence a specific estimated mobility range) can be controlled within the required limit as ions are being accumulated into the trapping region of the IMS device. Ions may be accumulated in the trapping region 3 substantially simultaneously to ions being ejected from the upstream low performance, high capacity ion trap. The transmission of ions between the upstream high capacity analytical ion trap and the IMS trapping region 3 is controlled by the attenuation lens during this process. Once ions have been accumulated in the IMS trapping region 3, the population may be released into the IMS device 5 and separated as previously described.

It is preferable to record a value representative of the attenuation of the ion population applied for each mass to charge ratio range during filling of the IMS trapping region 3. This value may be used to re-scale the intensity of the data recorded during the acquisition to represent the intensity of the incoming ion beam before attenuation. This enables the quantitative performance of the system to be maintained even though some ions have been discarded.

What is claimed is:

1. A method of analysing ions by ion mobility separation or mass separation comprising:
    providing an ion mobility separator separation region (IMS) and an ion trap for releasing packets of ions into the IMS;
    selecting a predetermined maximum charge desired to be released into the IMS in each packet of ions released from the ion trap into the IMS;
    releasing a first packet of ions from the ion trap;
    detecting the charge of ions in the first packet of ions using a detector;
    determining a difference between the charge detected by the detector and said predetermined maximum charge; and
    releasing a second, subsequent packet of ions from the ion trap into the IMS, wherein the formation of the second packet of ions is controlled based on the difference between the charge detected in the first packet of ions and the predetermined maximum charge, such that the charge of ions in the second packet of ions is substantially the same or less than said predetermined maximum charge.

2. The method of claim 1, wherein ions are permitted to enter and become trapped in said ion trap during ion accumulation periods, wherein the first packet of ions is accumulated within the ion trap over a first accumulation period and the second packet of ions is accumulated within the ion trap over a second accumulation period, and wherein the duration of the second accumulation period is selected or altered relative to the first accumulation period based on the difference between the charge of the ions detected in the first packet of ions and the predetermined maximum charge.

3. The method of claim 1, wherein ions are directed into the ion trap at an ion fill rate and are trapped in said ion trap during ion accumulation periods, wherein the first packet of ions is accumulated within the ion trap at a first ion fill rate and the second packet of ions is accumulated in the ion trap at a second ion fill rate, and wherein the second fill rate is selected or altered relative to the first fill rate based on the difference between the charge of the ions detected in the first packet of ions and the predetermined maximum charge.

4. The method of claim 1, wherein only a portion of the ions in the ion trap is ejected during the release of each packet of ions from the ion trap, and wherein the size of the portion ejected in said second packet of ions is selected or altered relative to the size of the portion ejected in the first packet of ions based on the difference between the charge of the ions detected in the first packet of ions and the predetermined maximum charge.

5. The method of claim 1, wherein the first packet of ions passes through the IMS and to the detector; wherein ions are driven through the IMS by an electric field, and wherein the electric field is varied with time such that ions in the first packet of ions are driven through the IMS at a high speed and corresponding ions in the second packet of ions are driven through the IMS at a low speed.

6. The method of claim 1, wherein a mass analyser is provided downstream of the IMS and upstream of the detector for mass analysing ions that have passed through the IMS, wherein the mass analyser is operated in a first mode such that the first packet of ions is substantially unattenuated by the mass analyser or wherein the first packet of ions bypasses the mass analyser and then passes to the detector; and wherein the mass analyser is operated in a second mode such that the second packet of ions is attenuated by the mass analyser during mass analysis therein or wherein the second packet of ions does not bypass the mass analyser.

7. The method of claim 1, wherein a mass analyser and the detector are provided downstream of the IMS, wherein the first packet of ions is directed to the detector without passing to the mass analyser; and wherein the second packet of ions is directed to the mass analyser.

8. The method of claim 1, wherein said detector is provided upstream of said IMS and said first packet of ions is released from said ion trap to said detector.

9. The method of claim 1, further comprising detecting the charge of ions in the second packet of ions using a detector; determining a difference between the charge of the ions detected in the second packet of ions and the predetermined maximum charge; and releasing a third, subsequent packet of ions from the ion trap to the IMS; wherein the formation of the third packet of ions is controlled based on the difference between the charge detected in the second packet of ions and the predetermined maximum charge, such that the charge of ions in the third packet of ions is substantially the same or less than said predetermined maximum charge.

10. The method of claim 1, wherein the predetermined maximum charge is the maximum amount of charge of ions within a predetermined range of drift times through the IMS that is desired to be pulsed into the IMS in a packet of ions; wherein the first packet of ions is detected by the detector after the ions have passed through the IMS, wherein the detector determines the amount of charge of ions in the first packet of ions that have drift times within said predetermined range of drift times, and wherein this detected charge is compared to the predetermined maximum charge and the comparison is used to control the formation of the second packet of ions such that ions in the second packet of ions that have drift times within the predetermined range of drift times have a total charge that is substantially the same or less than the predetermined maximum charge.

11. The method of claim 1, wherein the predetermined maximum charge is the maximum amount of charge of ions within a predetermined range of drift times through the IMS that is desired to be pulsed into the IMS in a packet of ions; wherein ions having said predetermined range of drift times are assumed to have a predetermined range of mass to charge ratios; wherein the first packet of ions is mass analysed and the total charge of ions within this packet having said predetermined range of mass to charge ratios is detected; and wherein this detected charge is compared to the predetermined maximum charge and the comparison is used to control the formation of the second packet of ions such that the ions in the second packet of ions that have drift times within the predetermined range of drift times have a total charge that is substantially the same or less than the predetermined maximum charge.

12. A method of analysing ions by ion mobility separation or mass separation comprising:
providing an ion mobility separator separation region (IMS) and an ion trap for releasing packets of ions into the IMS;
selecting a predetermined maximum charge desired to be released into the IMS in each packet of ions released from the ion trap;
directing ions from an ion source to a detector and detecting the rate at which charge is received at the detector due to ions from the ion source being detected;
directing ions from the ion source into the ion trap and trapping the ions only during an ion accumulation period;
selecting the duration of the ion accumulation period or controlling the attenuation of ions travelling towards the ion trap during the accumulation period such that the charge of the ions trapped within the ion trap is substantially the same or less than said predetermined maximum charge; and
releasing the ions from the ion trap into the IMS.

13. The method of claim 12, wherein said detector is provided upstream of said IMS.

14. The method of claim 1, wherein said predetermined maximum charge is a total charge desired to be pulsed into the IMS for all ions in a packet of ions.

15. The method of claim 1, comprising operating a first mode of operation wherein first electric field conditions are applied within the IMS such that ions passing through the IMS separate according to their ion mobilities or operating a second mode of operation wherein second electric field conditions are applied within the IMS such that ions passing through the IMS separate according to their mass to charge ratios.

16. An ion mobility spectrometer or mass spectrometer comprising:
an ion mobility separator separation region (IMS), an ion trap for releasing packets of ions into the IMS, and a detector; and
control means arranged and adapted to:
release a first packet of ions from the ion trap;
detect the charge of ions in the first packet of ions using the detector;
determine a difference between the charge detected by the detector and a predetermined maximum charge desired to be released into the IMS in each packet of ions released from the ion trap into the IMS; and
release a second, subsequent packet of ions from the ion trap into the IMS, wherein the formation of the second packet of ions is controlled based on the difference between the charge detected in the first packet of ions and the predetermined maximum charge, such that the charge of ions in the second packet of ions is substantially the same or less than said predetermined maximum charge.

17. An ion mobility spectrometer or mass spectrometer comprising:
an ion source, an ion mobility separator separation region (IMS), an ion trap for releasing packets of ions into the IMS, and a detector; and
control means arranged and adapted to:
direct ions from the ion source to the detector and detect the rate at which charge is received at the detector due to ions from the ion source being detected;
direct ions from the ion source into the ion trap and trap the ions only during an ion accumulation period; and
select the duration of the ion accumulation period or control the attenuation of ions travelling towards the ion trap during the accumulation period such that the charge of the ions trapped within the ion trap is substantially the same or less than a predetermined maximum charge desired to be released into the IMS in each packet of ions released from the ion trap; and
release the ions from the ion trap into the IMS.

18. The method of claim 12, wherein said predetermined maximum charge is a total charge desired to be pulsed into the IMS for all ions in a packet of ions.

19. The method of claim 12, comprising operating a first mode of operation wherein first electric field conditions are applied within the IMS such that ions passing through the IMS separate according to their ion mobilities or operating a second mode of operation wherein second electric field conditions are applied within the IMS such that ions passing through the IMS separate according to their mass to charge ratios.

* * * * *